United States Patent [19]

Pich et al.

[11] Patent Number: 4,632,843
[45] Date of Patent: Dec. 30, 1986

[54] PROCESS FOR THE PREPARATION OF SOLID PHARMACEUTICAL PRODUCTS

[75] Inventors: Claus H. Pich; Thomas Moest, both of Moorrege, Fed. Rep. of Germany

[73] Assignee: BASF Aktiengesellschaft, Ludwigshafen, Fed. Rep. of Germany

[21] Appl. No.: 581,714

[22] Filed: Feb. 21, 1984

[30] Foreign Application Priority Data

Feb. 23, 1983 [DE] Fed. Rep. of Germany ....... 3306250

[51] Int. Cl.$^4$ ........................ A61K 9/48; A61K 33/14
[52] U.S. Cl. ........................................ 427/3; 156/600; 424/16; 424/19; 424/22; 424/35; 424/37; 514/951; 514/963; 514/965
[58] Field of Search .............. 427/3; 156/600; 424/16, 424/22, 35, 19, 37; 514/951, 963, 965

[56] References Cited

U.S. PATENT DOCUMENTS

| | | | |
|---|---|---|---|
| 2,853,420 | 9/1958 | Lowey | 424/37 |
| 2,996,431 | 8/1961 | Barry | 424/7.1 |
| 3,072,533 | 1/1963 | Johnson | 514/951 |
| 3,433,872 | 3/1969 | Ritter et al. | 514/963 |
| 3,854,480 | 12/1974 | Zaffaroni | 604/892 |
| 3,874,907 | 4/1975 | Gardon et al. | 427/3 |
| 3,909,444 | 9/1975 | Anderson et al. | 427/3 |
| 4,123,382 | 10/1978 | Morse et al. | 427/3 |
| 4,259,315 | 3/1981 | Lippmann et al. | 424/35 |
| 4,289,795 | 9/1981 | Bogentoft et al. | 427/3 |
| 4,361,546 | 11/1982 | Stricker et al. | 424/19 |
| 4,367,217 | 1/1983 | Gruber et al. | 424/19 |
| 4,386,120 | 5/1983 | Sato et al. | 427/3 |
| 4,479,911 | 10/1984 | Fong | 427/3 |

FOREIGN PATENT DOCUMENTS

| | | | |
|---|---|---|---|
| 799930 | 11/1968 | Canada | 427/3 |
| 942667 | 2/1974 | Canada | 604/892 |
| 137432 | 11/1983 | Netherlands . | |

OTHER PUBLICATIONS

H. P. Fiedler, Lexikon der Hilfsstoffe fur Pharmazie, Kosmetik und angrenzende Gebiete, 2nd edition, Editio Cantor K.G., D-7960 Aulendorf, 1981, vols. I and II.
Hagers Handbuch der Pharmazeut. Praxis, 4th edition, published by Springer, Berlin-Heidelberg-New York 1967-1980, vol. VI, part B.
Thesis by Beer, Techn. University of Munich, Jan. 19, 1981.
S. Sarig et al., J. Appl. Chem. Biotechnol., 28 (1978) 10, 663-667.
M. A. Belyshev et al., khim. prom. 6, (1977), 455-459.

*Primary Examiner*—Ronald W. Griffin
*Attorney, Agent, or Firm*—Keil & Weinkauf

[57] ABSTRACT

A process for the preparation of solid pharmaceutical products, wherein, in a first step, spherical single crystals of a pharmaceutical active compound or assistant are prepared by agitating a saturated aqueous, organic or organic-aqueous solution in high speed stirred crystallizers or draft-tube crystallizers at 50–500 revolutions per minute and seeding the solution with finely ground seed crystals of particle size less than 100 μm, while ensuring that at the time of addition of the seed crystals and during the growth thereof the solution is at all times only minimally supersaturated, this being achieved by slow cooling at a rate of not more than 50 K/h or corresponding slow evaporation of the solution, and in a second step the resulting spherical single crystals with diameters of 0.1–3 mm, preferably 0.5–2 mm, are separated from the solution, dried at 40°–200° C., compounded, where appropriate, with suitable pharmaceutical assistants or, if the single crystals serve as assistants, with suitable pharmaceutical active compounds, and then converted to solid pharmaceutical products by coating, tableting or filling into hard gelatin capsules.

2 Claims, No Drawings

PROCESS FOR THE PREPARATION OF SOLID PHARMACEUTICAL PRODUCTS

Dust-free spherical particles with a narrow particle size spectrum (i.e. with little scatter in diameter) are of oarticular interest for the preparation of solid drugs for oral administration. Such particles are easily pourable and can therefore be very accurately metered volumetrically; this is of great importance in, for example, the filling of hard gelatine capsules. Because of the spherical surface of the particles, the areas of contact between particles are small, so that caking of particles virtually does not occur. The danger of demixing, which always exists in granular products with a broad particle size spectrum, is greatly reduced.

The coating of these particles is an important factor. In contrast to sharp-edged crystals and to agglomerates of irregular shape, such particles can be uniformly provided with a great variety of coatings, without agglomeration occurring. Moreover, less of the coating substance is needed in order to achieve the desired properties such as neutral flavor, resistance to gastric juice, retardation or stabilization.

The rounded particles, either untreated or after-treated, i.e. coated, in the manner described, can be advantageously administered direct or after having been filled into hard gelatine capsules.

Essentially, two processes are known in the art for the preparation of such spherical particles, also referred to as pellets. Round particles can be produced by agglomerating fine angular primary particles, the agglomerates being subsequently rounded mechanically by plastic deformation or abrasion. An alternative process is to coat angular starter cores with adhesive solution and powder until they become round.

Both processes have disadvantages. Control of particle size is in most cases impossible. A broad particle size spectrum results and oversize and undersize particles have to be sieved out. Moreover, the particles are porous and often have little strength, so that they are pressure-sensitive and undesirable dust is easily produced by abrasion. Moreover, with neither process can pure substances be prepared, since additional substances such as adhesives and fillers have to be incorporated.

It is an object of the present invention to avoid the above disadvantages of the prior art.

We have found that this object is achieved by a process for the preparation of solid pharmaceutical products, wherein, in a first step, spherical single crystals of a pharmaceutical active compound or assistant are prepared by agitating a saturated aqueous, organic or organic-aqueous solution in high speed stirred crystallizers or draft-tube crystallizers at 50–500 revolutions per minute and seeding the solution with finely ground seed crystals of particle size less than 100 $\mu$m, while ensuring that at the time of addition of the seed crystals and during the growth thereof the solution is at all times only minimally supersaturated, this being achieved by slow cooling at a rate of not more than 50 K/h or corresponding slow evaporation of the solution, and in a second step the resulting spherical single crystals with diameters of 0.1–3 mm, preferably 0.5–2 mm, are separated from the solution; dried at 40°–200° C., compounded, where appropriate, with suitable pharmaceutical assistants or, if the single crystals serve as assistants, with suitable pharmaceutical active compounds, and then converted to solid pharmaceutical products by coating, tableting or filling into hard gelatin capsules.

The preparation of spherical single crystals, especially of potassium chloride, is known per se (cf. Thesis by Beer, Technical University of Munich, of 19.1.81; S. Sarig, N. Eidelmann, A. Glasner and J. A. Epstein, J. of appl. Chem. Biotechnol. 28 (1978) 10, 663–667; M. A. Belyshev, G. P. Baranov, V. A. Postnikov and V. A. Ryabkov, khim. prom. 6, (1977), 455–459; Netherlands Pat. No. 137,432). However, these crystals have not been proposed for use in the pharmaceutical industry even though, as explained above, there was an urgent need.

For the purposes of the present invention, spherical particles are not only strictly spherical particles but also particles without plane surfaces and without sharp edges which have a ratio of maximum diameter to minimum diameter of not more than 3:1 and preferably of less than 1.5:1. In such cases, the particle size quoted relates to the minimum diameter.

The term pharmaceutical active compound does not require explanation. It is, as the words imply, a compound which exhibits a pharmaceutical action and which at the same time has sufficiently slight side-effects that it can be used as a drug.

The term "pharmaceutical assistant" is explained in more detail in, for example, the following publications: H. P. Fiedler, Lexikon der Hilfsstoffe für Pharmazie, Kosmetik und angrenzende Gebiete, 2nd edition, Editio Cantor K. G., D-7960 Aulendorf, 1981, volumes I and II; Hagers Handbuch der Pharmazeut. Praxis, 4th edition, published by Springer, Berlin-Heidelberg-New York 1967–1980, volume VII, part B; and in the usual pharmacopeias (DAB, PhEur, BP, USP etc.). Of course a precondition for the suitability of a substance for the purpose of the present invention is its ability to crystallize. Accordingly polymers are ruled out. On the other hand, in principle any crystallizable compound, especially those which crystallize easily ( in coarse crystals) can be employed. Moreover, it is obvious that the active compounds must be soluble, to an adequate degree for the particular therapeutic purpose, in the saliva or at least upon passage through the gastro-intestinal tract.

The term "soluble, crystalline, pharmaceutical assistant" inter alia includes, for example, fillers such as lactose, Ca phosphate, common salt, urea and mannitol, the constituents of effervescent mixtures, such as sodium bicarbonate and citric acid or tartaric acid, flavor improvers such as sugars (e.g. glucose or sucrose), sugar substitutes (sorbitol or xylitol) and synthetic sweeteners (eg saccharin and cyclamate).

For the purposes of the present invention, solid pharmaceutical products are granules, tablets, film tablets, effervescent tablets, coated tablets and hard gelatine push-fit capsules. Their preparation is familiar to a skilled worker and is also described in, for example, the above standard works. The spherical single crystals to be employed according to the invention are pellets and can be marketed as such, either directly or after the active compound particles have been coated with assistants or the assistant particles have been coated with active compounds, where appropriate in a plurality of alternating layers; however, the products can also be brought into a handy form, i.e. a form in which they can be metered conveniently and precisely, by tableting (molding with binders) or by being filled into capsules.

The spherical single crystals are prepared in a conventional manner (cf. the literature cited at the outset)

in high-speed stirred crystallizers or draft-tube crystallizers, by cooling or concentrating aqueous, organic or aqueous-organic solutions. The critical factor is that the crystal particles should undergo adequate movement, so that the ordered growth of the crystals is disturbed by the relative movement of the particles and the solution. In the simplest case, vigorous stirring is employed. The required speed of stirring depends on the geometry of the stirrer and of the vessel and is in general of the order of magnitude of from 50 to 1.000, preferably from 100 to 600, revolutions/ min. Moreover, it is necessary to seed the saturated solution with seeding crystals. These are advantageously finely ground crystals, ie. the particle diameter is less than 300 μm, preferably less than 100 μm. At the time of addition of the seeding crystals, and during their growth, the solution must at all times only exhibit minimum supersaturation; this ensures that a narrow particle size spectrum is maintained. This minimum supersaturation is achieved by slow cooling (not more than 50, preferably less than 10, in particular less than 5, K/h) or by appropriately slow evaporation of the solution.

The preparation of the crystals may be carried out batchwise or continuously. The results of experiments on the effect of the intensity of stirring, on the solids content of the crystal suspension and on the residence time can be extrapolated from batchwise operation to continuous operation. It is economically advantageous if the spherical crystallization is coupled with the purification—in any case needed in most instances—of the substances by recrystallization.

In the continuous process, the particle size is in the main controlled through the residence time. In batchwise operation, the particle size depends not only on the crystallization time but also on the number of seeding crystals. If the diameter of the seeding crystals is less than 30 μm, the weight ratio of seeding crystals to substance to be crystallized out is in general of the order of magnitude 9f from 1:1,000 to 1:1,000,000, preferably from 1:10,000 to 1:100,000. Hard, pressure-resistant and abrasion-resistant, non-porous spherical particles (single crystals) with diameters of from 0.1 to 3 mm, preferably from 0.5 to 2.0 mm, are obtained. These are pure substances, free from admixtures.

The advantages of the spherical shape of the particles very particularly come into play if the particles are provided with a coating. Compared to angular particles, such a coating is very uniform, substantially less coating material is needed and the desired effect (for example resistance to gastric juice, controlled—for example linearly retarded—release of active compound (which may or may not be coupled with a multi-phase action of the coated tablet) or merely masking of an unpleasant taste) is achieved more effectively and more reliably.

The nature of the relevant coating materials is described in the literature cited above in relation to pharmaceutical assistants, and is familiar to a skilled worker.

Because of their high stability to deformation forces, the spherical particles produced as above can be molded to form tablets which after oral administration disintegrate in the stomach initially into the original undamaged particles. This is especially important in the case of retard tablets and gastric juice-resistant tablets, since these, because of their size, frequently do not pass the pylorus and are kept back in the stomach. Accordingly, not only hard gelatine capsules but also tablets can be employed for medically desirable multi-unit dose administration.

The Examples which follow illustrate the invention.

In the Examples, no attention was given to yield. In continuous operation, using pure starting substance, the yield is quantitative; under other conditions, it depends on the purity of the starting material, the desired purity of the end product and—in batchwise operation—on the amount of labor expended, and is from 10 to 100%, preferably from 50 to 100%.

EXAMPLE 1

(a) 40 liters of a saturated aqueous potassium chloride solution heated to 40° C. were stirred vigorously in a commercial 50 liter stirred kettle equipped with a propeller stirrer and double jacket.

After the addition of 50 mg of potassiqm chloride crystal seeds of particle size less than 30 um, the solution was allowed to cool to 20° C. at a rate of 3 K/h, with constant stirring at a speed of $n=300$ min$^{-1}$.

The resulting crystals were diluted with a small amount of cold water to prevent secondary crystallization and were immediately filtered off on a suction filter, rinsed with a small amount of cold water and dried in a fluidized bed drier, the feed air temperature being 60° C.

The product consisted of colorless spherical crystals of particle diameter from about 0.4 to about 1.2 mm, the distribution curve showing a pronounced maximum at 0.7 mm.

(b) The spherical potassium chloride crystals thus obtained were continuously coated, in a fluidized bed spray granulator, with a 6.5% strength by weight solution of ethylcellulose in ethano.1 The. specific viscosity of the ethylcellulose was 10 mPa.s. The polymer solution contained 20%, based on polymer weight, of dibutyl phthalate as plasticizer. The total amount of coating polymer was 7%, based on the coated potassium chloride. The fluidized bed coating was so controlled that the product temperature was from 28 to 30° C.

The spherical potassium chloride pellets thus provided with a retarding coating were mixed with 0.5% of highly disperse silica. The product lent itself to easy and accurate filling into hard gelatine capsules on conventional equipment.

Table 1 shows a comparison of potassium chloride release from different retarded particles.

A was based on the spherical pellets employed according to the invention, which had been prepared as described and been provided with 7% of coating.

B contained conventional cubic potassium chloride of appropriately selected particle size distribution. It was coated with ethylcellulose using the same recipe and process as in the case of A.

C corresponded to B but the amount of coating was 13% by weight.

T shows the theoretical straight line for exact zero-order release.

TABLE 1

Release in %
The release was determined as described for the paddle method in USP XX.

| Formulation | Time (h) | | | |
|---|---|---|---|---|
| | 1 | 2 | 4 | 8 |
| A | 21 | 39 | 64 | 95 |
| B | 49 | 72 | 93 | 97 |
| C | 30 | 48 | 63 | 84 |

TABLE 1-continued

| | Release in % The release was determined as described for the paddle method in USP XX. | | | |
|---|---|---|---|---|
| | Time (h) | | | |
| Formulation | 1 | 2 | 4 | 8 |
| T | 12.5 | 25 | 50 | 100 |

The comparison shows that the spherical particles to be used according to the invention approximate relatively closely to the ideal conditions of zero-order release, whereas conventionally prepared potassium chloride shows substantial deviations from this behavior. Even varying the amount of coating does not make it possible to bring cubic potassium chloride to the high retardation level of the spherical crystal products.

(c) A mixture of the retarded, spherical potassium chloride obtained above (65 parts by weight), directly tabletable calcium hydrogen phosphate dihydrate (15 parts by weight), microcrystalline cellulose (12.5 parts by weight), sodium starch glycolate (7 parts by weight) and magnesium stearate (0.5 part by weight, in the stated proportions, was molded on a conventional rotary tableting press to give tablets of size 18×8 mm, weighing 1,000 mg each. The tablets obtained had a tensile strength of 70–90 N (Schleuniger test apparatus) and a coefficient of variation $V_{rel}$ of the mean tablet weight of less than 1%. The disintegration time was less than 2 minutes. The release of potassium chloride from the retarded pellets of the fast-disintegrating tablets (A in Table 2) differed only slightly from the values given in Table 1 for pellets according to the invention which had not been tableted.

On similar tableting of retarded cubic potassium chloride corresponding to B in Table 1, using an identical tablet recipe, the tablets produced had a maximum tensile strength of 70 N (Schleuniger test apparatus) and a substantially greater weight fluctuation, with $V_{rel}=1.6\%$.

The release of potassium chloride from the pellets of the disintegrated tablets (B in Table 2) is again substantially faster than from the retarded cubic potassium chloride on which they are based (B in Table 1).

TABLE 2

| | Release in % | | | |
|---|---|---|---|---|
| | Time (h) | | | |
| Formulation | 1 | 2 | 4 | 8 |
| A | 24 | 44 | 67 | 95 |
| B | 61 | 80 | 97 | 98 |

Accordingly, the retarded spherical potassium chloride pellets of the invention provided the simplest way of obtaining tablets with medically desirable type of potassium chloride release. On the other hand, conventionally processed potassium chloride under the stated conditions gave tablets with a minimal, unacceptable retard effect. Progressive improvement was only achievable with substantial additional expense.

EXAMPLE 2

5 liters of a saturated iron-II sulfate solution, heated to 50° C., were stirred in a vacuum-tight 6 liter draft tube crystallizer in which d:D:H=0.6:1:2 (d=diameter of flow tube, D=diameter of vessel, H=height of vessel), the crystallizer being equipped with an angled paddle stirrer and double jacket; stirring was sufficiently intense to ensure constant vertical circulation around the draft tube (n=about 200 min$^{-1}$).

After having added 10 mg of iron-II sulfate crystal seeds of particle size less than 30 um, the pressure was slowly reduced, in such a way that to start with about 100 ml/h of water was condensed out in a cold trap. The pressure was then reduced further and at the same time the temperature was progressively lowered to 0° C. at a rate of 20 K/h.

The crystals formed were filtered off on a suction filter, rinsed with a small amount of later at 0° C. and dried in an oven at 50° C. and 20 mbar. The product consisted of pale green spherical crystals of particle diameter range from 0.5 to 1.3 mm, the distribution curve showing a pronounced maximum at 0.8 mm.

The spherical iron-II sulfate thus obtained was continuously coated in a fluidized bed spray granulator with a solution of hydroxypropylmethylcellulose phthalate in a 3:7 isopropanol/methylene chloride mixture; the concentration of the solution was 7% by weight. The total amount of coating polymer was 12% by weight, based on the coated iron-II sulfate. 20% by weight, based on polymer, of dibutyl phthalate were added to the polymer solution as a plasticizer.

The fluidized bed coating was so controlled that the product temperature remained in the range from 26 to 28° C.

The resulting gastric juice-resistant spherical iron-II sulfate pellets were mixed with 0.5% of highly disperse silica. The product lent itself to easy and accurate filling into hard gelatine capsules on conventional equipment.

The gastric juice resistance was tested by the method of the European Pharmacopeia.

The advantage of the gastric juice-resistant iron-II sulfate pellets prepared according to the invention becomes evident on comparison with corresponding pellets prepared by a conventional process (Comparative Experiment 1).

COMPARATIVE EXPERIMENT 1

Finely crystalline iron-II sulfate was agglomerated and molded, using a 10% strength aqueous solution of hydroxypropylmethylcellulose (specific viscosity 6 mPa.s), in a coating kettle until round granule particles had been formed (cf. W. A. Ritschel, Die Tablette, Editio Cantor K.G., D-7960 Aulendorf, 1966, pages 212 and 213). After the granules had been dried, they were sieved, in two passes, to give a product with particle size range from 0.3 to 1.19 mm. The yield of this fraction was 63%. Larger aggl-omerates, of which a high proportion had formed and which had sizes of up to 10 mm diameter, had to be recomminuted and re-agglomerated, together with the fines of less than 0.3 mm, in an additional process step.

The pellets formed had an irregular, only approximately spherical shape and a porous structure. They contained 94% of iron-II sulfate.

A similar gastric juice-resistant coating operation to that described in Example 2, using 12% by weight of hydroxypropylmethylcellulose phthalate, based on total weight, and carried out in a fluidized bed unit, did not give a gastric juice-resistant product. Only when 16% of coating was used did the test for gastric juice resistance according to the European Pharmacopeia prove positive.

The bulk density, determined according to DIN 53,468, was 0.65 g/ml, which is 14.5% lower than for the product obtained according to the invention in Example 2 (namely 0.76 g/ml).

The determinable amount of iron-II sulfate per unit volume was thus, overall, about 23%

$$\left(\text{namely,} = 100 - 0.94 \times \frac{(100 - 16)}{(100 - 12)} \times \frac{0.65}{0.76} \times 100\right)$$

greater in the case of the novel spherical iron-II sulfate particles with gastric juice-resistant coating than for conventionally prepared gastric juice-resistant iron-II sulfate pellets.

This result was confirmed in a comparative capsule-filling test with hard gelatine push-fit capsules of size 00. The ratio of the amounts filled into the capsules, expressed as iron-II sulfate, was on average 628 mg: 486 mg. Accordingly, the novel iron-II sulfate particles gave an effective dosage advantage of 22.6%.

EXAMPLE 3

40 liters of a saturated solution of citric acid in ethanol heated to 45° C. were stirred vigorously in a commercial 50 liter stirred kettle equipped with a propeller stirrer and double jacket.

After the addition of 100 mg of citric acid crystal seeds of particle size less than 30 μm, the solution was allowed to cool slowly to 20° C. at a rate of 6 K/h, with constant stirring at a speed of $n=300$ min$^{-1}$.

The resulting crystals were diluted with a small amount of cold ethanol and were immediately filtered off on a suction filter, rinsed with a small amount of cold ethanol and dried in a fluidized bed drier, the feed air temperature being 60° C.

The product consisted of colorless spherical crystals with particle diameter from 0.3 to 1.0 mm, the distribution curve showing a pronounced maximum at 0.5 mm.

A mixture of the spherical citric acid particles, thus obtained, with potassium bicarbonate, directly tabletable cane sugar (instant sugar) and polyethylene glycol 6000 in the weight ratio of 1:1:1:0.1 was directly molded on a rotary tableting press to give tablets weighing 7.75 g and having a diameter of 28 mm. The effervescent tablets thus obtained had a tensile strength of greater than 90 N (Schleuniger test apparatus; tablets tested immediately after having been produced), an abrasion of 0.5% (Roche Friabilator, about 100 g, 300 revolutions) and a coefficient of variation of the mean tablet weight of 0.7%. The disintegration time measured according to the European Pharmacopeia was less than 3 min.

The important advantages of the effervescent tablet recipe containing the novel spherical citric acid particles become clear on comparison with the properties of effervescent tablets which are based on conventional commercial citric acid also having a mean particle size of 0.5 mm (Comparative Experiment 2).

COMPARATIVE EXPERIMENT 2

Using, other than the citric acid, identical recipe constituents and identical mixing and molding methods, effervescent tablets having a tensile strength of only 50–70 N, an abrasion of 2.8% and a coefficient of variation of the mean tablet weight of 1.9% were obtained. On exact adherence to the method of the European Pharmacopeia, the disintegration time was in some cases greater than 8 min and accordingly no longer conformed to the required limit of 5 min. Over this long time, the particle agglomerates containing incorporated citric acid persisted and these agglomerates showed exceptionally poor solubility.

Accordingly, the use of spherical citric acid in the preparation of effervescent tablets leads not only to an improvement in the mechanical properties of the tablets but also permits meeting the requirements of the Pharmacopeia, which cannot be met with conventional citric acid.

EXAMPLE 4

40 liters of a saturated aqueous magnesium sulfate solution heated to 70° C. were stirred vigorously ($n=300$ min$^{-1}$) in a commercial vacuum-tight 50 liter stirred kettle equipped with a propeller stirrer and double jacket.

After addition of 50 mg of magnesium sulfate crystal seeds of particle size less than 30 μm, the pressure was reduced cautiously until the solution boiled gently. The reduced pressure was then so adjusted, at a constant temperature of 70° C., that 2 liters of water per hour separated out in a condenser. After 10 hours, the process was stopped and the resulting crystals were immediately filtered off on a suction filter and rinsed with a small amount of water at 70° C. They were dried in a paddle drier at 120° C.

The product consisted of colorless spherical crystals of particle size range from 0.5 to 2 mm. The maximum of the distribution curve was at 1.0 mm.

The spherical magnesium sulfate thus obtained was sprayed in a rotating perforated drum (Accela Cota 24 from Manesty, Liverpool, having an 0.3 mm laser beam-perforated drum) with a 20% strength by weight aqueous hydroxypropylmethylcellulose solution (specific viscosity 3 mPa.s) heated to 40° C., spraying being effected with a two-material nozzle. The air feed temperature was 60° C.

The air throughput was controlled so that on applying 50 ml/min of the coating solution, the product assumed a temperature of 33°–35° C. The total amount of coating was 10%, based on coated magnesium sulfate. The spherical magnesium sulfate pellets having a coating soluble in gastric juice were easy to meter and had an absolutely neutral taste.

COMPARATIVE EXPERIMENT 3

Conventional magnesium sulfate particles coated in exactly the same way presented problems.

During preparation, using identical conditions but employing sieved-out commercial magnesium sulfate of corresponding particle size spectrum, a considerable tendency to agglomeration was observed and could only be prevented by drastically slowing down the process. On reducing the coating spraying rate and the air feed temperature, the time required doubled.

10% of coating, based on coated particles, moreover did not suffice to give a neutral taste. Only after application of 15% of coating was the bitter taste of magnesium sulfate no longer perceptible.

In the conventional process, the costs of coating are in total substantially greater than when using the spherical magnesium sulfate according to the present invention, having a gastric juice-soluble coating. Conventional preparation is, by comparison, uneconomical, since it requires 50% more coating and the duration of the process is, in total, 3 times as long.

EXAMPLE 5

In a 6 liter draft tube crystallizer as in Example 2, 5 liters of a saturated solution of acetylsalicylic acid in ethanol, heated to 40° C., were stirred so intensely as to ensure constant vertical circulation around the draft tube (n=about 150 min$^{-1}$). After addition of 5 mg of acetylsalicylic acid crystal seeds of particle size less than 100 μm, the batch was steadily cooled to 20° C. at a rate of 4 K/h, while maintaining the draft tube conditions.

The resulting crystal suspension was mixed with a small amount of ethanol to prevent secondary crystallization, and the crystals were filtered off on a suction filter and rinsed with a small amount of ethanol. They were dried in a fluidized bed drier at an air feed temperature of 60° C.

The product consisted of colorless spherical crystals having a particle size range of from 0.5 to 1.5 mm, with a pronounced maximum of the distribution curve at 0.9 mm.

This spherical acetylsalicylic acid was continuously coated with ethylcellulose, from a solution in ethanol, in a fluidized bed spray granulator. The ethylcellulose had a specific viscosity of 10 mPa.s, the concentration of the solution being 7% by weight. 25% by weight, based on polymer, of dibutyl phthalate was added as a plasticizer to the polymer solution. The total amount of coating polymer was 6% by weight, based on the coated product.

The fluidized bed coating process was so controlled that the product temperature remained in the range from 26° to 28° C.

The retarded spherical acetylsalicylic acid particles were mixed with 0.5% of highly disperse silica. The product lent itself to easy and accurate filling into hard gelatine capsules on conventional equipment.

The release of the acetylsalicylic acid from the retarded spherical particles described above, in a paddle apparatus according to USP XX (using 437 mg of retarded spherical product, with water as the medium) was 41% after 2 hours.

Identically coated commercial acetylsalicylic acid under the same conditions gave 86% release after 2 hours.

Accordingly, the spherical base particles permit a marked improvement in the release kinetics.

We claim:

1. A process for the preparation of solid pharmaceutical products, wherein, in a first step, sperical single crystals of a pharmaceutical active compound or assistant are prepared by agitating a saturated aqueous, organic or organic-aqueous solution in high speed stired crystallizers or draft-tube crystallizers at 50–1000 revolutions per minute and seeding the solution with finely ground seed crystals of particle size less than 300 μm, while ensuring that at the time of addition of the seed crystals and during the growth thereof the solution is at all times only minimally supersaturated, this being achieved by slow cooling at a rate of not more than 50 K/h or corresponding slow evaporation of the solution, and in a second step the resulting spherical single crystals with diameters of 0.1-3 mm are separated from the solution, dried at 40°–200° C., compounded with suitable pharmaceutical assitants or, if the single crystals serve as assistants, with suitable pharmaceutical active compounds, and then coverting to solid pharmaceutical products bycoating, tableting or filling into hard gelatin capsules.

2. Solid pharmaceutical pellets containing one or more active compounds or assistants in the form of spherical single crystal with diameters of 0.1-3 mm.

* * * * *

UNITED STATES PATENT AND TRADEMARK OFFICE
CERTIFICATE OF CORRECTION

PATENT NO. : 4,632,843

DATED : December 30, 1986

INVENTOR(S) : PICH et al.

It is certified that error appears in the above-identified patent and that said Letters Patent is hereby corrected as shown below:

In the Claims:

Column 10, line 15: [sperical] should be: spherical

Column 10, line 37: [crystal] should be: crystals

Signed and Sealed this

Thirty-first Day of March, 1987

Attest:

DONALD J. QUIGG

Attesting Officer      Commissioner of Patents and Trademarks